United States Patent
Zuffi et al.

(10) Patent No.: US 8,012,717 B2
(45) Date of Patent: Sep. 6, 2011

(54) METHOD FOR THE PRODUCTION OF CLADRIBINE

(75) Inventors: Gabriele Zuffi, Varese (IT); Simone Monciardini, Varese (IT)

(73) Assignee: Explora Laboratories S.A. (CH)

( * ) Notice: Subject to any disclaimer, the term of this patent is extended or adjusted under 35 U.S.C. 154(b) by 292 days.

(21) Appl. No.: 12/002,248

(22) Filed: Dec. 14, 2007

(65) Prior Publication Data

US 2010/0291632 A1    Nov. 18, 2010

(30) Foreign Application Priority Data

Dec. 15, 2006    (EP) ..................................... 06026046

(51) Int. Cl.
C12P 19/40    (2006.01)
C12P 19/38    (2006.01)

(52) U.S. Cl. ........................................... 435/88; 435/87
(58) Field of Classification Search ........................ None
See application file for complete search history.

(56) References Cited

U.S. PATENT DOCUMENTS 5,208,327 A    5/1993    Chen
6,252,061 B1    6/2001    Sampath et al.
2002/0052491 A1    5/2002    Gerszberg et al.
2004/0039190 A1    2/2004    Gupta et al.
2006/0094869 A1    5/2006    Komatsu et al.

FOREIGN PATENT DOCUMENTS

EP    0173059 A2    3/1986
EP    1439220 A1    7/2004
WO    2004/028462 A2    4/2004

OTHER PUBLICATIONS

Mikhailopulo et al. "Synthesis of 2-chloro-2'-deoxyadenosine by Microbiological Transglycosylation", Nucleosides & Nucleotides, vol. 12, Nos. 3 and 4, 1993, pp. 417-422.
Tarasiuk et al. "Stability of 2-chloro-2'-deoxyadenosine at Various pH and Temperature", Archivum Immunologiae et Therapiae Experimentalis, vol. 42, No. 1, 1994, pp. 13-15.
Votruba et al. "Synthesis of 2-deoxy-beta-D-Ribonucleosides and 2,3-dideoxy-beta-D-pentofuranosides on Immobilized Bacterial Cells", Collection of Czechoslovak Chemical Communications, vol. 59, No. 10, 1994, pp. 2303-2330.

*Primary Examiner* — Tekchand Saidha
*Assistant Examiner* — Md. Younus Meah
(74) *Attorney, Agent, or Firm* — Akerman Senterfitt

(57) ABSTRACT

A method for producing cladribine (2-chloro-2' deoxyadenosine) comprising the steps of: a) reaction of 2-deoxyuridine with 2-chloroadenine, in the presence of uridine phosphorylase (UPase) and purine nucleoside phosphorylase (PNPase) in an aqueous reaction medium possibly containing up to 40% v/v of an aprotic dipolar solvent, to obtain cladribine dissolved in said reaction medium; b) isolation of the cladribine by precipitation by means of concentration and alkalinisation of the reaction medium up to pH 11.5-12.5.

25 Claims, No Drawings

METHOD FOR THE PRODUCTION OF CLADRIBINE

FIELD OF APPLICATION

The present invention refers to a method for producing cladribine (2-chloro-2'-deoxyadenosine).

More specifically, the invention refers to a method for producing cladribine by means of a transglycosylation reaction.

PRIOR ART

As is known, cladribine (2-chloro-2'-deoxyadenosine) is a molecule used as antineoplastic drug in the treatment of leukaemia and other neoplasias and has the following formula (I):

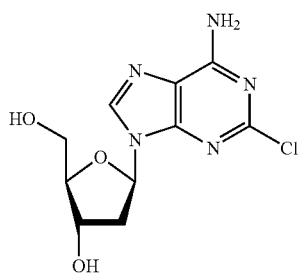

Various synthesis methods of Cladribine have been described; among these we highlight the following.

The U.S. patent application Ser. No. 5,208,327 (Chen, R. H. K., filed on 16 Apr. 2002) describes a synthesis method of the cladribine starting from guanosine in 7 chemical synthesis steps with the use of numerous reagents.

The U.S. Pat. No. 6,252,061 describes a synthesis which foresees a direct halogenation of 2,6-diaminopurine deoxyribose in a mixture of protic and aprotic solvents, in the presence of a Lewis acid and an organic nitrite. The synthesis foresees a column purification of the final product.

The international patent application WO 2004/028462 describes a synthesis for direct halogenation of 2'-deoxyguanosine followed by a chromatographic separation for every intermediate.

The patent application EP 173 059 describes a synthesis which foresees a condensation of a purine base and an adequately protected deoxyribose.

The U.S. patent application No. 2002/0052491 describes a synthesis beginning from Chloroadenine and adequately protected deoxyribose, with improved yields with respect to EP 173,059 and elimination of the column purification step.

The U.S. patent application No. 2004/0039190 describes a reaction between adequately protected chloroadenine and adequately protected deoxyribose, with improved yields with respect to U.S. 2002/0052491.

Cladribine production by means of chemical synthesis processes has significant limitations, since such processes often consist of multiple-stage reaction, which comprise protection and deprotection reactions starting from compounds which are costly and/or hard to find on the market, and sometimes involve non-stereospecific reactions (i.e. which lead to the production of the final product in both α and β conformations). Such processes are therefore long and costly, and yields are rarely satisfying. These process types, therefore, by their nature, do not lend themselves to be employed on an industrial scale.

On the other hand, enzymatic reactions, such as for example glycosylation and transglycosylation reactions, better lend themselves for use on an industrial level and the variety of enzymes available in nature permit selecting the desired stereospecificity and regioselectivity of the reaction. Such reactions usually require, then, a final step of purification (for example by means of precipitation or filtration) of the product mixture in order to isolate, to the desired purity level, the product from the enzyme, the unreacted substrate and from possible reaction co-products (for example isomers).

Another advantage of the enzymatic reactions with respect to the synthesis reactions is the fact that the enzymes which are used, in addition to being available on the market, are also easily found in large quantities and at low cost, in nature, for example from the cultivation of bacterial cells.

It is therefore possible to cultivate the bacteria which produce the enzyme of interest and isolate the enzyme from the bacterial cells. Alternatively, the enzymatic reactions can be carried out by using whole bacterial cells, the latter solution usually leading to less efficient reactions (with therefore lower yields) which are however more convenient and economical.

The enzymatic reactions can then be classified into free enzyme reactions and immobilised enzyme reactions. In the first case, the enzymes are added to the reaction mixture, while in the second case the enzymes (or the bacterial cells) are immobilised on appropriate carriers.

The immobilisation of the enzymes or bacterial cells leads to the advantage of not having to separate the enzymes from the product mixture at the end of the reaction and of allowing, therefore, to recover the enzymes or the cells and reuse them for a subsequent reaction. The immobilisation moreover enables to carry out the reactions continuously or in batches, therefore obtaining higher yields and attaining greater suitability for use on an industrial scale.

Finally, the enzymatic reactions can be optimised by means of genetic manipulation of the bacteria which produce the enzyme. Such manipulation is usually aimed to confer a greater enzyme yield or enzymatic activity. It can regard, nevertheless, other factors such as the suppression of the production of other possible enzymes by the microorganism, the stereoselectivity or regioselectivity of the enzyme of interest, etc.

Enzymatic reactions for producing cladribine are described in numerous articles and patents. Among these we highlight the following.

In Michailopulo, I A et al (1993) Nucleosides & Nucleotides, 13 (3&4) 417-422, the biochemical synthesis of Cladribine is described beginning from chloroadenine and deoxyguanosine in the presence of E. coli cells.

The U.S. patent application No. 2006/0094869 describes a reaction between chloroadenine and deoxyribose-1-phosphate in the presence of the purified purine nucleoside phosphorylase (PNP) enzyme.

The abovementioned documents describe production processes of the cladribine which while advantageous with respect to the chemical methods set forth above, nevertheless involve various drawbacks, including low yields, substrates (for example deoxyguanosine and deoxyribose 1-phosphate) which are hard to find and finally process steps (such as the final isolation on column chromatography) of difficult industrial application.

The latter step of isolation and purification of the final product has generally been the most problematic for the entire production process of the cladribine through enzymatic means.

The technical problem underlying the present invention is therefore that of making available a method for the production of cladribine which permits obtaining product yields which are equal to or greater than those of the prior art, starting from economical, easy-to-find raw materials, and which is at the same time economically advantageous and permits an easy isolation of the final product.

SUMMARY OF THE INVENTION

One such problem is resolved according to the present invention by a method for producing cladribine (2-chloro-2'-deoxyadenosine) comprising the steps of:
a) reaction of 2-deoxyuridine with 2-chloroadenine, in the presence of uridine phosphorylase (UPase) and purine nucleoside phosphorylase (PNPase) in an aqueous reaction medium possibly containing up to 40% v/v of an aprotic dipolar solvent, to obtain cladribine dissolved in said reaction medium;
b) isolation of the cladribine by precipitation by means of concentration and alkalinisation of the reaction medium up to a pH of 11.5-12.5.

The enzymes UPase and PNPase can be present in the reaction medium in the form of free enzymes or enzymes immobilised on adequate carriers, or they can be produced in situ by cells which produce them, which in turn can be present in the reaction medium in a free form or in immobilised form.

When producer cells of UPase enzymes or producer cells of PNPase enzymes are used, or when producer cells of both the enzymes UPase and PNPase are used, such cells are preferably immobilised by adsorption onto a weak anion exchange resin, in particular onto a weak anion exchange resin having amine functional groups. Particularly preferred is a resin chosen from the group comprising the Dowex MWA1 (Dow Chemical), Diaion WA30 (Mitsubishi), Duolite A7®, Amberlite FPA54®, Amberlyst 21 and Duolite A568® (Rohm & Haas) resins. The latter resin is particular preferred for the objects of the present invention.

The process for obtaining the immobilisation of UPase and/or PNPase producer cells onto weak anion exchange resins is described in application EP 06005241 of the same Applicant.

According to an embodiment of the invention, the aforesaid cells are cells of the *Escherichia coli* species.

Particularly preferred is the use of *Escherichia coli* cells of the DH5alpha strain, transformed by means of plasmid vectors having the sequences reported in Sequence Id No. 1 and 2.

The aforesaid aprotic dipolar solvent is generally represented by dimethylformamide or by dimethylsulphoxide or mixtures thereof and is preferably dimethylformamide.

The aforesaid alkalinisation step is preferably carried out so as to obtain a pH equal to about 12.

Preferably the 2-deoxyuridine and the 2-chloroadenine are reacted in a molar ratio ranging from 1:1 to 3:1, advantageously about 2:1.

The reaction between 2-deoxyuridine and 2-chloroadenine is generally carried out in a buffered medium, for example by means of a phosphate buffer, at a pH in the range of 6.5-8.5, preferably 7.3-7.8.

The reaction is generally conducted at a temperature in the range of 50-70° C., suitably at about 60° C.

According to a further aspect of the present invention, the reaction between 2-deoxyuridine and 2-chloroadenine is carried out by gradually adding, to the aqueous reaction medium buffered to pH 7-8 and containing the enzymes and the 2-deoxyuridine, a solution of 2-chloroadenine in a mixture of water and aprotic dipolar solvent, at a speed such that the 2-chloroadenine remains in solution until it has been converted into the final product, i.e. such that no precipitation of 2-chloroadenine occurs during the reaction.

The aforesaid solution of 2-chloroadenine is preferably prepared by suspending the 2-chloroadenine in an aprotic dipolar solvent and adding a concentrated solution of an alkaline hydroxide until a complete dissolution of the 2-chloroadenine is obtained.

The aprotic dipolar solvent in question is preferably dimethylformamide and the alkaline hydroxide is preferably KOH, used in a concentration in the range of 20-30% w/v.

The addition is foreseen of an aqueous solution of a strong acid at the same time as the addition of the 2-chloroadenine solution, at such an extent as to maintain the pH of the reaction mixture between 6.5 and 8.5, preferably between 7.3 and 7.8.

As the strong acid, mineral acids such as HCl or $H_3PO_4$ can be used, or organic acids can be used such as, for example, citric acid.

The aforesaid steps of concentration and alkalinisation of the reaction medium at the end of the reaction can be carried out in any order but preferably the alkalinisation is carried out first, followed by the concentration.

When immobilised enzymes or immobilised cells are used, before proceeding with the alkalinisation and concentration steps, a filtration or centrifugation step is carried out to remove the immobilised enzymes or immobilised cells from the reaction mixture.

The precipitate obtained at the end of such steps is filtered and possibly recrystallised with a hydroalcoholic mixture, for example with 95:10 ethanol/water v/v.

Thanks to the method according to the present invention, it is possible to carry out a stereospecific reaction, which leads to the formation of high yields of the desired product only in its β configuration. Moreover, the method according to the present invention resolves the drawbacks mentioned in the prior art and permits isolating the cladribine produced in an extremely simple, effective and economical manner, thus making the method easily transferable to an industrial production. In particular, the isolation step of the cladribine from the other components of the reaction mixture is brilliantly executed with a simple variation of the pH, without having to resort to costly chromatographic separations, and it permits obtaining the product with a high level of purity.

DETAILED DESCRIPTION

As stated above, it is preferred to conduct the transglycosylation reaction according to the invention by using, rather than UPase and PNPase enzymes as such, immobilised Upase- and/or PNPase-producing cells. Such cells are preferably cells of genetically modified *Escherichia coli*, capable of expressing considerable quantities of UPase or PNPase.

Such cells were obtained in the following manner:
1. Construction of Recombinant Strains Expressing the UPase Enzyme or PNPase Enzyme The recombinant strains were constructed by transforming a host strain of *Escherichia coli* with a plasmid with a high number of copies containing the gene of interest and a marker for the selection.

The host strain used is the DH5alpha strain, found easily on the market (GIBCO-BRL) and extensively described in the literature. It is a strain derived from *Escherichia coli* K12 and therefore considered of safety class 1, thus adapted for a use of industrial type.

The gene UdP, coding for the UPase enzyme, and the gene deoD, coding for the PNPase enzyme, have already been well described in literature and their sequences are known and available at the EMBL databank, characterised by the accession numbers X15679 for UdP and M60917 for deoD.

Genes were amplified by means of PCR (polymerase chain reaction) using suitably prepared synthetic primers.

The genes were inserted, using the appropriate restriction enzymes KpnI and SalI for UdP and EcoRI and SalI for deoD, in the zone of the polylinker of the plasmid with a high number of pUC18 copies, well characterised in literature and commercially available.

In both plasmids (that containing the UdP gene and that containing the deoD gene), the resistance to the kanamycin antibiotic was then inserted, obtained by means of digestion with the HindIII restriction enzyme of the pBSL14 plasmid, which is commercially available.

Finally, for both plasmids (that containing the UdP gene and that containing the deoD gene), the resistance to Ampicillin was destroyed through deletion, by means of digestion with the AvaII enzyme.

Unexpectedly, two sites recognised by the restriction enzyme AvaII were found, with the consequent formation of 3 plasmid fragments rather than the two expected, whereas in literature only one restriction site for this enzyme is reported.

The final plasmids were obtained by recovering the two larger fragments and eliminating the unnecessary fragment which had formed. The main characteristics of the new genetically modified strains are reported in the following table.

TABLE

| STRAIN | Host | Plasmid | Selection marker | Expressed protein | AmpR presence |
|---|---|---|---|---|---|
| EXP05/03 | DH5alpha | pUC18 | Kanamycin | UPase | No |
| EXP05/04 | DH5alpha | pUC18 | Kanamycin | PNPase | No |

The sequence of the plasmids pursuant to the preceding table are reported in the lists at the end of the description and in particular the sequence of the pUC18 plasmid containing the UdP gene corresponds to Sequence Id. No. 1 and the sequence of the pUC18 plasmid containing the deoD gene corresponds to Sequence. Id. No. 2.

2. Preparation of the Biocatalyst

The biocatalyst is prepared using genetically modified strains of *Escherichia coli* which are capable of over-expressing the phosphorylase activities due to the Uridine Phosphorylase and Purine Nucleoside Phosphorylase enzymes, in the specific case the strains EXP05/03 and EXP 05/04. The immobilisation of cell suspensions containing the UPase enzymatic activity and the PNPase enzymatic activity is prepared starting from a mixture of cell suspensions prepared so to have a ratio between the enzymatic activity due to the UPase enzyme and the enzymatic activity due to the PNPase enzyme in the range of 1:1-3:1. In this example, the immobilisation is described of a mixture of cell suspensions in which the ratio between the enzymatic activity due to the UPase enzyme and the enzymatic activity due to the PNPase enzyme is about 3:1.

About 20 (dry weight) grams of Rohm & Haas Duolite A568 resin is added to 200 ml of a mixture of cell suspensions composed of cells containing the UPase enzymatic activity (EXP05/03) in the measure of about 115 units/ml and of cells containing the PNPase enzymatic activity (EXP 05/04) in the measure of about 33 units/ml.

The mixture is held at room temperature with moderate stirring for 48 hours. The immobilisation mixture is then filtered. The resin is washed with water until clear washing waters are obtained (about 2 liters).

The resin with the immobilised enzymatic activities is then preserved at 4° C. in 0.1 M potassium phosphate buffer at pH 7.5.

3. Activity of the Resin with Immobilised Cells

The catalytic activity of the enzymes UPase and PNPase coupled in the resin with immobilised cells is determined with a transglycosylation reaction carried out using standardised conditions.

200 g or 400 g of solid carrier with immobilised cells containing the UPase enzymatic activity and the PNPase enzymatic activity (wet weight) as described in the preceding point is added to 10 ml of reaction mixture.

The reaction is carried out with the following solution: 40 mM arabinofuranosyluracil (Ara-U), 40 mM adenine, 30 mM monobasic potassium phosphate—pH 7.2, at a temperature thermostated at 60° C. After 60 minutes at 60° C., the reaction is stopped by diluting the reaction 1:50 in water. The percentage of adenine converted into arabinofuranosyladenine (ARA-A) is determined by analysing an aliquot of the reaction mixture with a high performance liquid chromatograph (HPLC) equipped with a Nucleosil 100-5 column (Macherey-Nagel) of 250×4.6 mm size, eluting with a 10 mM monobasic potassium phosphate buffer −6% methanol. The catalytic activity of the coupled UPase and PNPase enzymes (catalytic activity of transglycosylation) is expressed in units/wet g (micromoles per minute of Adenine converted to form ARA-A in the assay conditions/wet weight gram of cell paste) and is calculated with respect to the adenine conversion percentage.

4. Fermentation of the Cells Containing the UPase Enzymatic Activity or the PNPase Enzymatic Activity The recombinant strains EXP05/03 (coding for the UPase enzyme) and EXP05/04 (coding for the PNP enzyme) were separately fermented batchwise by using a fermenter with a useful volume of 15 liters, containing 15 of culture medium with the following composition (per liter):

13.3 g $KH_2PO_4$;
40 g soitone;
36 g yeast extract;
1.5 g $MgSO_4.7H2O$;
0.02 g kanamycin The fermenter was inoculated with about 150 ml of bacterial suspension which had previously been grown for about 24 h at 37° C. The fermentation was carried out using the following parameters: 37° C. temperature, mechanical stirring of about 250 r.p.m., air flow automatically controlled to hold the $pO_2$ value at 20% of the saturation concentration, pH controlled at 7+0.2 by means of the addition of a 10% ammonia solution or a 20% phosphoric acid solution.

Once the fermentation is terminated (completed in about 24 hours), the cell paste was collected for centrifugation, washed with 100 mM potassium phosphate buffer at pH 7.0, collected once again for centrifugation and preserved in the form of wet cell paste at a temperature of −20° C.

5. Determination of the Enzymatic Activities a) Determination of the Enzymatic Activity Due to the UPase Enzyme.

A known quantity (100 or 200 microliters) of suspension of the cells which express the UPase enzyme (EXP05/03), diluted 1:100 or 1:1000 as wet weight/volume in potassium phosphate buffer at pH 7.0-7.2, is added to 800 microliters of a 75 mM Uridine solution in 100 mM, pH 7.0-7.2 phosphate buffer, pre-incubated at 30° C. After exactly 5 minutes, the phosphorolysis reaction is stopped with the addition of 1 ml of HCl. An aliquot of the reaction mixture is analysed with a high performance liquid chromatograph (HPLC) equipped with a Nucleosil 100-5 column (Macherey-Nagel) of 250×4.6 mm size. The elution is carried out with a 10 mM monobasic potassium phosphate solution –6% methanol.

The enzymatic activity of the cell paste is expressed as units/gram of wet weight (micromoles transformed per minute per 1 gram of wet cell paste) and is calculated with respect to a standard curve constructed with the uracil quantities formed in the same assay conditions, using increasing quantities of the same cell paste.

b) Determination of the Enzymatic Activities Due to the PNPase.

A known quantity (100 or 200 microliters) of suspension of the cells which express the PNPase enzyme (EXP05/04), diluted 1:100 or 1:1000 as wet weight/volume in potassium phosphate buffer at pH 7.0-7.2, is added to 800 microliters of a 60 mM Inosine solution in 100 mM, pH 7.0-7.2 phosphate buffer, pre-incubated at 30° C. After exactly 10 minutes, the phosphorolysis reaction is stopped with the addition of 1 ml of HCl. An aliquot of the reaction mixture is analysed with a high performance liquid chromatograph (HPLC) equipped with a Nucleosil 100-5 column (Macherey-Nagel) of 250×4.6 mm size. The elution is carried out with a 10 mM monobasic potassium phosphate solution –6% methanol. The enzymatic activity of the cell paste is expressed as unit/gram of wet weight (micromoles transformed per minute per 1 gram of wet cell paste) and is calculated with respect to a standard curve constructed with the hypoxanthine quantities formed in the same assay conditions, using increasing quantities of the same cell paste.

6. Solubility of 2-Chloroadenine 0.42 g (equal to 2.5 mMoles) of 2-chloroadenine were suspended in 50 ml of DMF and heated while being stirred. Aliquots of DMF were added until a complete hot solubilisation was obtained. 100 ml of solvent were necessary to obtain the solubilisation of the 2-chloroadenine.

A solubilisation test was also carried out of 2-chloroadenine in 25% KOH in order to increase the solubilisation. 4.05 grams of 2-chloroadenine were resuspended in KOH being stirred. Aliquots of (25% w:v) KOH were added until complete solubilisation was obtained. Even after the addition of 100 ml of 25% KOH, the 2-chloroadenine remained practically undissolved. Even in very concentrated KOH the molecule was practically insoluble.

7. Reaction in 20% DMF

A transglycosylation reaction was carried out using 2-chloroadenine solubilised in DMF. 0.42 grams (equal to 2.5 mMoles) of 2-chloroAdenine were suspended and hot-solubilised while being stirred in 100 ml of DMF, up to boiling, obtaining a 25 mMolar solution.

To 25 ml of this solution, thermostated at 60° C., 80 ml were added of a solution of 18.75 mM 2'-d-Uridine and 37.5 mM $KH_2PO_4$ at pH 7.3 for the KOH, heated to 70° C. During the addition of this solution, there occurred the formation of precipitate which remained undissolved even by heating once again to boiling.

The test has been repeated by adding the 2'-d-Uridine/$KH_2PO_4$ solution dropwise. After a small addition, the formation of precipitate is noted, which is slowly dissolved by stopping the addition. The remainder of the solution was added at very small aliquots, allowing the situation to equilibrate.

Thus, a clear solution was obtained to which 5 grams of resin were added with immobilised cells with an activity of 5 units/wet gram of resin (measured as in point 3).

The final mixture had a 15 mM d-uridine concentration; 5 mM 2-chloroadenine; 30 mM $KH_2PO_4$; resin with of immobilised cells: 250 units/litre of reaction.

The reaction was followed by HPLC and after 3 hours there was the conversion of about 80% of the 2-chloroadenine into cladribine.

8. Reaction in DMF/KOH

To increase the solubility of the 2-chloroadenine in DMF, concentrated bases or acids were added and in both cases a greater solubilisation was obtained.

The acidic environment, however, can degrade the deoxynucleosides, therefore tests were only carried with the addition of concentrated KOH.

4.05 grams (equal to 24 mMoles) of 2-chloroAdenine were weighed and suspended in 50 ml of DMF. 30 ml of 25% KOH (w:v) were added. There remained a slight opalescence which disappeared with the addition of 10 ml of $H_2O$, obtaining a 266 mMolar solution. To this solution, thermostated at 60° C., 600 ml were added of a pH 7.3 solution containing 10.95 grams (equal to 48 mMoles) of 2'-d-uridine and 4 grams of KH2PO4 (equal to 30 mMoles). Incipient precipitation of the 2-chloroadenine was obtained.

The preparation of the two solutions was repeated. 30 wet grams of resin with immobilised cells were added (5 U/wet gram calculated as in point 3) to the 2'-d-Uridine solution, thermostated at 60° C.

The solution of 2-chloroadenine in DMF/KOH was very slowly added to this suspension, so to prevent the precipitation of the 2-chloroadenine. In this manner, if the addition occurred at an appropriate speed, most of the added 2-chloroadenine was transformed into Cladribine before reaching a concentration such to cause precipitation.

With the addition of the 2-chloroadenine in DMF/KOH, the pH of the reaction started to increase, and since the enzymatic activities functioned in optimal manner at physiological pH values, it was necessary to add hydrochloric acid to maintain the pH at the desired values.

At the end of the additions, there were the following concentrations:

35 mMolar 2-chloroadenine; 70 mMolar 2-deoxyuridine; 37.5 mM $KH_2PO_4$; resin with immobilised cells: 220 U/litre of reaction.

In these conditions, a conversion of 80% of the 2-chloroadenine into cladribine was obtained.

9. Reaction with Controlled Addition

After having carried out different preliminary optimisation tests, a reaction was carried out for preparing the Cladribine, adding the 2-chloroadenine substrate and the pH corrector in a controlled manner.

6.75 grams (equal to 40 mMoles) were weighed of 2-chloroadenine and were suspended while being stirred in 50 ml of DMF. Solubilisation occurred with the addition of 70 ml of 25% KOH (w:v), obtaining a perfectly clear solution with a 333 mMolar concentration. 18.25 grams (equal to 80 mMoles) of 2'-deoxyUridine and 4 grams (equal to 30 mMoles) of anhydrous monobasic potassium phosphate were added and solubilised in 600 ml of deionised water, obtaining a 133 mM concentration for the 2-deoxyuridine and 50 mM for $KH_2PO_4$. The pH was corrected to a value of 7.5 with 25% (w:v) KOH as required.

The 2'-deoxyUridine solution in phosphate buffer was loaded into a 1 litre reactor thermostated at 60° C. with mechanical stirring.

30 wet grams of just filtered resin with immobilised cells, prepared as in point 2, were added to the reactor.

The specific activity of the resin with immobilised cells (measured as reported in point 3) was 5 U/wet gram.

The solution of 2-chloroadenine in KOH/DMF was slowly added to the suspension of 2'-deoxyUridine in phosphate buffer and resin with immobilised cells. The addition was carried out by means of a peristaltic pump with silicone tube with 1.5 mm inner diameter, at a flow rate of about 1 ml/min (equal to 0.33 mMoles/minute).

To maintain the pH at optimal values, a 2N hydrochloric acid solution was added simultaneously to the solution of 2-chloroadenine in DMF/KOH, so to maintain the pH value in the range of 6.5-8.5, preferably in the range of 7.3-7.8.

The addition of 2N HCl was carried out with a peristaltic pump equipped with silicone tube with 1.5 mm inner diameter and flow rate of about 1 ml/min.

With respect to the final volume, there were the following concentrations:

50 mMolar 2-chloroadenine; 100 mMolar 2-deoxyuridine; 37.5 mM $KH_2PO_4$; resin with immobilised cells: 187.5 U/litre of reaction.

At the end of the addition, the reaction was filtered on paper. The resin was recovered and stored in 100 mM phosphate buffer at pH 7.4, at a temperature of 4° C., while the filtrate was processed for the isolation of the cladribine. In these conditions, about 80% of the 2-chloroadenine was converted into cladribine.

10. Reaction with Controlled Addition in DMSO

The same reaction pursuant to point 8 was carried out using the dimethylsulphoxide as solvent for the solubilisation of the 2-chloroadenine instead of the dimethylformamide.

5.4 grams (equal to 32 mMoles) of 2-chloroadenine were weighed and suspended while being stirred in 50 ml of DMSO. Solubilisation occurred with the addition of 70 ml of 25% (w:v) KOH, obtaining a perfectly clear solution with a 266 mMolar concentration of 2-chloroAdenine. 14.6 grams (equal to 64 mMoles) of 2'-deoxyuridine and 4 grams (equal to 30 mMoles) of anhydrous monobasic potassium phosphate were dissolved in about 600 ml of deionised water, obtaining a 106 mM for the 2-deoxyUridine and 50 mM for $KH_2PO_4$. The pH was corrected to a value of 7.5 with 25% (w:v) KOH as required.

The 2'-deoxyUridine solution in phosphate buffer was loaded into a 1 litre reactor thermostated at 60° C. with mechanical stirring.

30 wet grams of just filtered resin with immobilised cells, prepared as in point 2, were added to the reactor.

The specific activity of the resin with immobilised cells (measured as reported in point 3) was 5 U/wet gram.

The solution of 2-chloroadenine in KOH/DMF was then slowly added to the suspension of 2'-deoxyuridine in phosphate buffer and resin with immobilised cells. The addition was carried out by means of a peristaltic pump with a silicone tube with 1.5 mm inner diameter, at a flow rate of about 1 ml/min (equal to 0.26 mMoles/minute).

To maintain the pH at optimal values, a 2N hydrochloric acid solution was added simultaneously to the solution of 2-chloroadenine in DMF/KOH, so to maintain the pH value in the range of 6.5-8.5, preferably in the range of 7.3-7.8.

The addition of 2N HCl was carried out with a peristaltic pump equipped with silicone tube with 1.5 mm inner diameter and flow rate of about 1 ml/min.

With respect to the final volume, there would have been the following concentrations:

40 mMolar 2-chloroadenine; 80 mMolar 2-deoxyuridine; 37.5 mM $KH_2PO_4$; resin: 187.5 U/litre of reaction.

At the end of the addition, the reaction mixture was filtered on paper. The resin was recovered and stored in 100 mM phosphate buffer at pH 7.4, at a temperature of 4° C., while the filtrate was processed for the isolation of the cladribine. In these conditions, about 80% of the 2-chloroadenine was converted into cladribine.

11. Addition of Different Acids

The pH can be controlled and maintained constant around optimal values by also using phosphoric acid, in addition to hydrochloric acid, permitting the completion of the reaction without encountering problems of precipitation of the 2-chloroadenine. Equivalent results were obtained by using a solution of 5% phosphoric acid instead of 2N hydrochloric acid.

12. Recycling of the Resin

The resin with immobilised cells used for one reaction, after having been filtered and separated from the reaction mixture, was stored at 4° C. in phosphate buffer or immediately used for a subsequent reaction.

The resin with immobilised cells (prepared as in point 1) was used, with equivalent final yields, for at least 4 subsequent reactions.

The presence of DMF in the 2-chloroadenine solution, the relatively high temperature and the addition of concentrated acid and base solution did not cause drastic diminutions of the biocatalyst activity.

13. Purification Tests

The filtered reaction mixture was processed so to be able to isolate and purify the cladribine from the other components of the reaction.

The filtered reaction mixture was concentrated in a Rotavapor until the initial volume was reduced by about 3 times, and was transferred first at room temperature and then at 4° C. Precipitate was formed which was separated by filtration and which was composed essentially of unreacted 2-chloroadenine and by uracil formed during the reaction.

Precipitation tests were carried out on the resulting mother liquors by varying the pH value.

Tests were conducted at pH 4.0-7.0-10.0-12.0.

At an acidic pH, there was the formation of precipitate, which was formed only by inorganic salts.

At pH values 7.0 and 10.0, the precipitate was obtained composed essentially of cladribine and uracil, the latter in considerably quantities.

Only with the pH 12.0 test was a precipitate obtained, which was found to be cladribine with high purity. To increase the yield, the pH change was repeated on a solution which was 5 times more concentrated, a high purity product always being obtained.

By concentrating 10 times, a co-precipitation was obtained, essentially of cladribine and residual uracil.

The cladribine thus obtained was recrystallised under reflux conditions at 90° in 20 volumes of a $EtOH:H_2O$ mixture, obtaining an anhydrous product with high purity (greater than 99.0%). The quantitative yield of the cladribine after purification and recrystallisation is in the range of 4-5 grams for every litre of reaction mixture, both for the reactions with DMF and for those with DMSO.

In order to improve the process from an industrial standpoint, a test was carried out in which the bioconversion mixture was brought to pH 12.0 once the reaction had been terminated and the biocatalyst had been separated. Subsequently, the concentration of the solution was carried out by reducing the volume 5-6 times, obtaining precipitation. The precipitate was transferred cold and separated by filtration, resulting in cladribine with a high level of purity.

In this manner, the first concentration step and subsequent filtration were eliminated, simplifying the process, and a comparable quality product was obtained.

The invention claimed is:

1. A method for producing cladribine (2-chloro-2'-deoxy-adenosine) comprising the steps of:
   a) reaction of 2-deoxyuridine with 2-chloroadenine, in the presence of uridine phosphorylase (UPase) and purine nucleoside phosphorylase (PNPase) in an aqueous reaction medium optionally containing up to 40% v/v of an aprotic dipolar solvent, to obtain cladribine dissolved in said reaction medium;
   b) isolation of the cladribine by precipitation by means of concentration and alkalinisation of the reaction medium to reach a pH of between 11.5-12.5.

2. The method according to claim 1, wherein said UPase and PNPase enzymes are produced in situ by cells capable of producing them.

3. The method according to claim 2, wherein said Upase- and PNPase- producing cells are immobilised on a resin carrier.

4. The method according to claim 3, Wherein said carrier is composed of a weak anion exchange resin, onto which said cells are adsorbed.

5. The method according to claim 4, wherein said resin has amino functional groups and is chosen from the group comprising Dowex MWA1 (Dow Chemical), Diaion WA30 (Mitsubishi), Duolite A7®, Amberlite FPA54®, Amberlyst 21 and Duolite A568® (Rohm & Haas) resins.

6. The method according to claim 5, wherein said resin is Duolite A568® (Rohm & Haas).

7. The method according to claim 3, wherein said Upase- and PNPase-producing cells are *Escherichia coli* cells.

8. The method according to claim 7, wherein said cells are *Escherichia coli* cells transformed with a plasmid having nucleic acids comprising SEQ ID NO: 1 and 2.

9. The rnethod according to claim 1, wherein said aprotic dipolar solvent consists of dimethylformamide and/or dimethylsulphoxide.

10. The method according to claim 1, wherein the pH at the end of the alkalinisation step is about 12.

11. The method according to claim 1, wherein the 2-deoxyuridine and the 2-chloroadenine are reacted in a molar ratio ranging from 1:1 to 3:1.

12. The method according to claim 1, wherein the reaction between 2-deoxyuridine and 2-chloroadenine is carried out in a buffered medium at a pH in the range of 6.5-8.5.

13. The method according to claim 1, wherein the reaction between 2-deoxyuridine and 2-chloroadenine is conducted at a temperature in the range of 50-70° C.

14. The method according to claim 1, wherein the reaction between 2-deoxyuridine and 2-chloroadenine is carried out by gradually adding a solution of 2-chloroadenine in a water and aprotic dipolar solvent mixture to the aqueous reaction medium buffered to pH 6.5-8.5 and containing the enzymes and the 2-deoxyuridine.

15. The method according to claim 14, wherein said 2-chloroadenine solution is prepared by suspending the 2-chloroadenine in an aprotic dipolar solvent and adding a concentrated solution of an alkali hydroxide until the dissolution of the 2-chloroadenine is completed.

16. The method according to claim 15, wherein said aprotic dipolar solvent is dimethylformamide or dimethylsulphoxide and the alkaline hydroxide is KOH, used at a concentration in the range of 20-30% w/v.

17. The method according to claim 14, wherein the pH of the reaction mixture is maintained between 6.5-8.5 by adding an aqueous solution of a strong acid at the same time as the addition of the solution of 2-chloroadenine.

18. The method according to claim 17, wherein said strong acid is chosen between hydrochloric acid and phosphoric acid.

19. The method according to claim 1, wherein said concentration step follows said alkalinisation step.

20. The method according to claim 1, comprising the further steps of recovery of the precipitated cladribine by means of filtration and subsequent recrystallisation of the same.

21. The method according to claim 3, wherein said recrystallisation is carried out by a hydroalcoholic mixture.

22. The method according to claim 12, wherein the pH is in the range of 7.3-7.8.

23. The method according to claim 13, wherein the temperature is about 60° C.

24. The method according to claim 17, wherein the pH of the reaction mixture is maintained between 7.3-7.8.

25. The method of claim 21, wherein the hydroalcoholic mixture is 95:10 cthanol:water.

* * * * *

SEQUENCE LISTING

<160> NUMBER OF SEQ ID NOS: 2

<210> SEQ ID NO 1
<211> LENGTH: 4454
<212> TYPE: DNA
<213> ORGANISM: ARTIFICIAL
<220> FEATURE:
<223> OTHER INFORMATION: PLASMID
<220> FEATURE:
<221> NAME/KEY: GENE
<222> LOCATION: (49)..(843)
<223> OTHER INFORMATION: KANAMICINE RESISTANCE
<220> FEATURE:
<221> NAME/KEY: GENE
<222> LOCATION: (1285)..(2046)
<223> OTHER INFORMATION: UDP

<400> SEQUENCE: 1

| | | | | | |
|---|---|---|---|---|---|
| tgtaaaacga | cggccagtgc | caagcttggg | cgaaccccag | agtcccgctc | agaagaactc | 60 |
| gtcaagaagg | cgatagaagg | cgatgcgctg | cgaatcggga | gcggcgatac | cgtaaagcac | 120 |
| gaggaagcgg | tcagcccatt | cgccgccaag | ctcttcagca | atatcacggg | tagccaacgc | 180 |
| tatgtcctga | taacggtccg | ccacacccag | ccggccacag | tcgatgaatc | cagaaaagcg | 240 |
| gccattttcc | accatgatat | tcggcaagca | ggcatcgcca | tgggtcacga | cgagatcctc | 300 |
| gccgtcgggc | atccgcgcct | tgagcctggc | gaacagttcg | gctggcgcga | gcccctgatg | 360 |
| ctcttcgtcc | agatcatcct | gatcgacaag | accggcttcc | atccgagtac | gtgctcgctc | 420 |
| gatgcgatgt | ttcgcttggt | ggtcgaatgg | gcaggtagcc | ggatcaagcg | tatgcagccg | 480 |
| ccgcattgca | tcagccatga | tggatacttt | ctcggcagga | gcaaggtgag | atgacaggag | 540 |
| atcctgcccc | ggcacttcgc | ccaatagcag | ccagtccctt | cccgcttcag | tgacaacgtc | 600 |
| gagcacagct | gcgcaaggaa | cgcccgtcgt | ggccagccac | gatagccgcg | ctgcctcgtc | 660 |
| ttggagttca | ttcagggcac | cggacaggtc | ggtcttgaca | aaaagaaccg | ggcgcccctg | 720 |
| cgctgacagc | cggaacacgg | cggcatcaga | gcagccgatt | gtctgttgtg | cccagtcata | 780 |
| gccgaatagc | ctctccaccc | aagcggccgg | agaacctgcg | tgcaatccat | cttgttcaat | 840 |
| catgcgaaac | gatcctcatc | ctgtctcttg | atcagatctt | gatccctgc | gccatcagat | 900 |
| ccttggcggc | aagaaagcca | tccagtttac | tttgcagggc | ttcccaacct | taccagaggg | 960 |
| cgccccagct | ggcaattccg | gttcgcttgc | tgtccataaa | accgcccagt | ctagctatcg | 1020 |
| ccatgtaagc | ccactgcaag | ctacctgctt | tctctttgcg | cttgcgtttt | cccttgtcca | 1080 |
| gatagcccag | tagctgacat | tcatccgggg | tcagcaccgt | ttctgcggac | tggctttcta | 1140 |
| cgtgttccgc | ttcctttagc | agcccttgcg | ccctgagtgc | ttgcggcagc | gtgaagctag | 1200 |
| cggaattcga | gctcggtacc | cggggatcct | ctagagtcga | cctgcaggca | tgcaagcttg | 1260 |
| catgcctgca | ggtcgacaag | agaattacag | cagacgacgc | gccgcttcca | ccacgatttt | 1320 |
| caccgcatgg | ctttcggttt | gtttcatcgt | ctcagcattc | gggatctctt | gctgggtgcg | 1380 |
| gttaacgata | acacccgcta | ccataccggc | acgcaggccc | tgacttgcac | acatggtcag | 1440 |
| cagggttgca | gattccattt | catagttcat | tacgcccatc | gcctgccact | cttccataga | 1500 |
| acctttaaag | tgacgaacta | cgcgaccaga | gtaagtatcg | taacgttcct | gacctgggta | 1560 |
| gaaggtatca | gaagaagctg | tcacgccaac | gtgagttgtc | gcgccaatgg | atttcgcagc | 1620 |
| ttcaaccagc | gcagtcgtac | attcgaaatc | agcgacagcc | gggaattcca | gcggtgcgaa | 1680 |
| gtgcaggctc | gcgccatcca | gacggacaga | cgccgtggta | accaggacat | cacccacatt | 1740 |

-continued

```
aatatgcggc tgaatagcgc ccgttgtacc gatacgcagg aaggtgcgaa tgcccagctg   1800
tgccagctct tcaacagcaa tagaggtaga cgggccgccg ataccggtag agcagacgat   1860
aacaggttta ccatccagct ctgcacgcca ggtagtgaat tcgcggtgag atgccagctt   1920
aaccggctta tccatcagcg cggcgatctt ttccacacga tccgggtcgc cagggacgat   1980
ggcaagcgta gccccttgta atcgttttt agtgaggccg agatgaaaaa catcagactt    2040
ggacatggat ggtaccgagc tcgaattcgt aatcatggtc atagctgttt cctgtgtgaa   2100
attgttatcc gctcacaatt ccacacaaca tacgagccgg aagcataaag tgtaaagcct   2160
ggggtgccta atgagtgagc taactcacat taattgcgtt gcgctcactg cccgctttcc   2220
agtcgggaaa cctgtcgtgc cagctgcatt aatgaatcgg ccaacgcgcg gggagaggcg   2280
gtttgcgtat tgggcgctct tccgcttcct cgctcactga ctcgctgcgc tcggtcgttc   2340
ggctgcggcg agcggtatca gctcactcaa aggcggtaat acggttatcc acagaatcag   2400
gggataacgc aggaaagaac atgtgagcaa aaggccagca aaaggccagg aaccgtaaaa   2460
aggccgcgtt gctggcgttt ttccataggc tccgcccccc tgacgagcat cacaaaaatc   2520
gacgctcaag tcagaggtgg cgaaacccga caggactata agataccagg cgtttcccc    2580 ctggaagctc cctcgtgcgc tctcctgttc cgaccctgcc gcttaccgga tacctgtccg   2640
cctttctccc ttcgggaagc gtggcgcttt ctcatagctc acgctgtagg tatctcagtt   2700
cggtgtaggt cgttcgctcc aagctgggct gtgtgcacga accccccgtt cagcccgacc   2760
gctgcgcctt atccggtaac tatcgtcttg agtccaaccc ggtaagacac gacttatcgc   2820
cactggcagc agccactggt aacaggatta gcagagcgag gtatgtaggc ggtgctacag   2880
agttcttgaa gtggtggcct aactacggct acactagaag aacagtattt ggtatctgcg   2940
ctctgctgaa gccagttacc ttcggaaaaa gagttggtag ctcttgatcc ggcaaacaaa   3000
ccaccgctgg tagcggtggt ttttttgttt gcaagcagca gattacgcgc agaaaaaaag   3060
gatctcaaga agatcctttg atcttttcta cggggtctga cgctcagtgg aacgaaaact   3120
cacgttaagg gattttggtc atgagattat caaaaaggat cttcacctag atccttttaa   3180
attaaaaatg aagttttaaa tcaatctaaa gtatatatga gtaaacttgg tctgacagtt   3240
accaatgctt aatcagtgag gcacctatct cagcgatctg tctatttcgt tcatccatag   3300
ttgcctgact ccccgtcgtg tagataacta cgatacggga gggcttacca tctggcccca   3360
gtgctgcaat gataccgcga gacccacgct caccggctcc agatttatca gcaataaacc   3420
agccagccga aagggccgag cgcagaagtg gtcctccgat cgttgtcaga agtaagttgg   3480
ccgcagtgtt atcactcatg gttatggcag cactgcataa ttctcttact gtcatgccat   3540
ccgtaagatg cttttctgtg actggtgagt actcaaccaa gtcattctga aatagtgta    3600 tgcggcgacc gagttgctct tgcccggcgt caatacggga taataccgcg ccacatagca   3660
gaactttaaa agtgctcatc attggaaaac gttcttcggg gcgaaaactc tcaaggatct   3720
taccgctgtt gagatccagt tcgatgtaac ccactcgtgc acccaactga tcttcagcat   3780
cttttacttt caccagcgtt tctgggtgag caaaaacagg aaggcaaaat gccgcaaaaa   3840
agggaataag ggcgacacgg aaatgttgaa tactcatact cttcctttt caatattatt     3900 gaagcattta tcagggttat tgtctcatga gcggatacat atttgaatgt atttagaaaa   3960
ataaacaaat aggggttccg cgcacatttc cccgaaaagt gccacctgac gtctaagaaa   4020
ccattattat catgacatta acctataaaa ataggcgtat cacgaggccc tttcgtctcg   4080
cgcgtttcgg tgatgacggt gaaaacctct gacacatgca gctcccggag acggtcacag   4140
```

| | |
|---|---|
| cttgtctgta agcggatgcc gggagcagac aagcccgtca gggcgcgtca gcgggtgttg | 4200 |
| gcgggtgtcg gggctggctt aactatgcgg catcagagca gattgtactg agagtgcacc | 4260 |
| atatgcggtg tgaaataccg cacagatgcg taaggagaaa ataccgcatc aggcgccatt | 4320 |
| cgccattcag gctgcgcaac tgttgggaag ggcgatcggt gcgggcctct tcgctattac | 4380 |
| gccagctggc gaaaggggga tgtgctgcaa ggcgattaag ttgggtaacg ccagggtttt | 4440 |
| cccagtcacg acgt | 4454 |

```
<210> SEQ ID NO 2
<211> LENGTH: 4393
<212> TYPE: DNA
<213> ORGANISM: ARTIFICIAL
<220> FEATURE:
<223> OTHER INFORMATION: PLASMID
<220> FEATURE:
<221> NAME/KEY: GENE
<222> LOCATION: (438)..(1232)
<223> OTHER INFORMATION: KANAMICINE RESISTANCE
<220> FEATURE:
<221> NAME/KEY: GENE
<222> LOCATION: (1277)..(1977)
<223> OTHER INFORMATION: DEOD

<400> SEQUENCE: 2
```

| | |
|---|---|
| tgtaaaacga cggccagtgc caagcttgca tgcctgcagg tcgactctag aggatccccg | 60 |
| ggtaccgagc tcgaattccg ctagcttcac gctgccgcaa gcactcaggg cgcaagggct | 120 |
| gctaaaggaa gcggaacacg tagaaagcca gtccgcagaa acggtgctga ccccggatga | 180 |
| atgtcagcta ctgggctatc tggacaaggg aaaacgcaag cgcaaagaga agcaggtag | 240 |
| cttgcagtgg gcttacatgg cgatagctag actgggcggt tttatggaca gcaagcgaac | 300 |
| cggaattgcc agctggggcg ccctctggta aggttgggaa gccctgcaaa gtaaactgga | 360 |
| tggctttctt gccgccaagg atctgatggc gcagggatc aagatctgat caagagacag | 420 |
| gatgaggatc gtttcgcatg attgaacaag atggattgca cgcaggttct ccggccgctt | 480 |
| gggtggagag gctattcggc tatgactggg cacaacagac aatcggctgc tctgatgccg | 540 |
| ccgtgttccg gctgtcagcg caggggcgcc cggttctttt tgtcaagacc gacctgtccg | 600 |
| gtgccctgaa tgaactccaa gacgaggcag cgcggctatc gtggctggcc acgacgggcg | 660 |
| ttccttgcgc agctgtgctc gacgttgtca ctgaagcggg aagggactgg ctgctattgg | 720 |
| gcgaagtgcc ggggcaggat ctcctgtcat ctcaccttgc tcctgccgag aaagtatcca | 780 |
| tcatggctga tgcaatgcgg cggctgcata cgcttgatcc ggctacctgc ccattcgacc | 840 |
| accaagcgaa acatcgcatc gagcgagcac gtactcggat ggaagccggt cttgtcgatc | 900 |
| aggatgatct ggacgaagag catcagggc tcgcgccagc cgaactgttc gccaggctca | 960 |
| aggcgcggat gcccgacggc gaggatctcg tcgtgaccca tggcgatgcc tgcttgccga | 1020 |
| atatcatggt ggaaaatggc cgcttttctg gattcatcga ctgtggccgg ctgggtgtgg | 1080 |
| cggaccgcta tcaggacata gcgttggcta cccgtgatat tgctgaagag cttggcggcg | 1140 |
| aatgggctga ccgcttcctc gtgctttacg gtatcgccgc tcccgattcg cagcgcatcg | 1200 |
| ccttctatcg ccttcttgac gagttcttct gagcgggact ctggggttcg cccaagcttg | 1260 |
| catgcctgca ggtcgactta ctcttttatcg cccagcagaa cggattccag tgcgattttg | 1320 |
| atcatgtcgt tgaaggtagt ctgacgctca gcggcagtgg tctgctcgtg agtgcggatg | 1380 |
| tggtcagata cggtgcagat ggtcagggct ttcgcgccaa attctgcagc gacgccgtag | 1440 |
| ataccagccg cttccatttc cacgccgaga atgccgtatt tttccatcac gtcgaacatt | 1500 |

```
tcgccgtccg gagagtagaa caggtcagcg gagaacaggt tacccacgcg agcatcaata   1560
cccagtgctt tagctgcatc tactgcgtta cgcaccatgt cgaagtcagc gatagcggca   1620
aagtcatggt ctttaaaacg gatgcggtta actttggaat cggtgcaggc acccataccg   1680
ataacgacgt cgcgcagttt tacgtgcggc agaactgcgc cacaggaacc cacgcggata   1740
attttcttca cgccgaaatc ggtgatcagt tctttggtgt agatggagca ggacgggata   1800
cccataccgt gacccattac ggaaattttg cggcctttgt aagtaccggt gaagcccagc   1860
ataccgcgaa cgttgttcac ttcacgggca tcttcaagga aagtttcagc aatatacttc   1920
gcacgcagcg ggtcgcctgg catcaaaact acgtcagcga aatcgcccat ttctgcatta   1980
atgtgtgggg tagccatgga agaattcgta atcatggtca tagctgtttc ctgtgtgaaa   2040
ttgttatccg ctcacaattc cacacaacat acgagccgga agcataaagt gtaaagcctg   2100
gggtgcctaa tgagtgagct aactcacatt aattgcgttg cgctcactgc ccgctttcca   2160
gtcgggaaac ctgtcgtgcc agctgcatta atgaatcggc caacgcgcgg ggagaggcgg   2220
tttgcgtatt gggcgctctt ccgcttcctc gctcactgac tcgctgcgct cggtcgttcg   2280
gctgcggcga gcggtatcag ctcactcaaa ggcggtaata cggttatcca cagaatcagg   2340
ggataacgca ggaaagaaca tgtgagcaaa aggccagcaa aaggccagga accgtaaaaa   2400
ggccgcgttg ctggcgtttt tccataggct ccgcccccct gacgagcatc acaaaaatcg   2460
acgctcaagt cagaggtggc gaaacccgac aggactataa agataccagg cgtttccccc   2520
tggaagctcc ctcgtgcgct ctcctgttcc gaccctgccg cttaccggat acctgtccgc   2580
ctttctccct tcgggaagcg tggcgctttc tcatagctca cgctgtaggt atctcagttc   2640
ggtgtaggtc gttcgctcca agctgggctg tgtgcacgaa ccccccgttc agcccgaccg   2700
ctgcgcctta tccggtaact atcgtcttga gtccaacccg gtaagacacg acttatcgcc   2760
actggcagca gccactggta acaggattag cagagcgagg tatgtaggcg gtgctacaga   2820
gttcttgaag tggtggccta actacggcta cactagaaga acagtatttg gtatctgcgc   2880
tctgctgaag ccagttacct tcggaaaaag agttggtagc tcttgatccg gcaaacaaac   2940
caccgctggt agcggtggtt tttttgtttg caagcagcag attacgcgca gaaaaaaagg   3000
atctcaagaa gatcctttga tcttttctac ggggtctgac gctcagtgga acgaaaactc   3060
acgttaaggg attttggtca tgagattatc aaaaaggatc ttcacctaga tcctttaaa    3120
ttaaaaatga gttttaaat caatctaaag tatatatgag taaacttggt ctgacagtta   3180
ccaatgctta atcagtgagg cacctatctc agcgatctgt ctatttcgtt catccatagt   3240
tgcctgactc cccgtcgtgt agataactac gatacgggag ggcttaccat ctggccccag   3300
tgctgcaatg ataccgcgag acccacgctc accggctcca gatttatcag caataaacca   3360
gccagccgga agggccgagc gcagaagtgg tcctccgatc gttgtcagaa gtaagttggc   3420
cgcagtgtta tcactcatgg ttatggcagc actgcataat tctcttactg tcatgccatc   3480
cgtaagatgc ttttctgtga ctggtgagta ctcaaccaag tcattctgag aatagtgtat   3540
gcggcgaccg agttgctctt gcccggcgtc aatacgggat aataccgcgc cacatagcag   3600
aactttaaaa gtgctcatca ttggaaaacg ttcttcgggg cgaaaactct caaggatctt   3660
accgctgttg agatccagtt cgatgtaacc cactcgtgca cccaactgat cttcagcatc   3720
ttttactttc accagcgttt ctgggtgagc aaaaacagga aggcaaaatg ccgcaaaaaa   3780
gggaataagg gcgacacgga aatgttgaat actcatactc ttcctttttc aatattattg   3840
aagcatttat cagggttatt gtctcatgag cggatacata tttgaatgta tttagaaaaa   3900
```

-continued

```
taaacaaata ggggttccgc gcacatttcc ccgaaaagtg ccacctgacg tctaagaaac    3960
cattattatc atgacattaa cctataaaaa taggcgtatc acgaggccct ttcgtctcgc    4020
gcgtttcggt gatgacggtg aaaacctctg acacatgcag ctcccggaga cggtcacagc    4080
ttgtctgtaa gcggatgccg ggagcagaca agcccgtcag ggcgcgtcag cgggtgttgg    4140
cgggtgtcgg ggctggctta actatgcggc atcagagcag attgtactga gagtgcacca    4200
tatgcggtgt gaaataccgc acagatgcgt aaggagaaaa taccgcatca ggcgccattc    4260
gccattcagg ctgcgcaact gttgggaagg gcgatcggtg cgggcctctt cgctattacg    4320
ccagctggcg aaaggggggat gtgctgcaag gcgattaagt tgggtaacgc cagggttttc    4380
ccagtcacga cgt                                                       4393
```